US010493690B2

United States Patent
Jaunet et al.

(10) Patent No.: US 10,493,690 B2
(45) Date of Patent: *Dec. 3, 2019

(54) METHOD FOR THE ADDITIVE MANUFACTURE OF A THREE-DIMENSIONAL OBJECT COMPRISING OR FORMING A COSMETIC COMPOSITION BY DIRECT PROJECTION USING A PHOTOACTIVATABLE MATERIAL

(71) Applicant: L'OREAL, Paris (FR)

(72) Inventors: Clément Jaunet, Velizy Villacoublay (FR); Sonia Lorente Gonzalez, Vincennes (FR)

(73) Assignee: L'OREAL, Paris (FR)

( * ) Notice: Subject to any disclaimer, the term of this patent is extended or adjusted under 35 U.S.C. 154(b) by 114 days.

This patent is subject to a terminal disclaimer.

(21) Appl. No.: 15/501,264

(22) PCT Filed: Aug. 5, 2015

(86) PCT No.: PCT/EP2015/068062
§ 371 (c)(1),
(2) Date: Feb. 2, 2017

(87) PCT Pub. No.: WO2016/020442
PCT Pub. Date: Feb. 11, 2016

(65) Prior Publication Data
US 2018/0186065 A1  Jul. 5, 2018

(30) Foreign Application Priority Data

Aug. 5, 2014 (FR) ...................................... 14 57619

(51) Int. Cl.
*B29C 39/12* (2006.01)
*B29C 41/22* (2006.01)
(Continued)

(52) U.S. Cl.
CPC .............. *B29C 64/112* (2017.08); *A61K 8/85* (2013.01); *A61K 8/92* (2013.01); *A61Q 1/04* (2013.01);
(Continued)

(58) Field of Classification Search
CPC ..... B29C 39/023; B29C 39/025; B29C 39/12; B29C 39/123; B29C 41/22; B29C 64/112;
(Continued)

(56) References Cited

U.S. PATENT DOCUMENTS

2010/0304100 A1* 12/2010 Fong ...................... G03F 7/0037
428/205
2015/0366327 A1* 12/2015 LaHood, Sr. ......... B29C 64/165
264/109

FOREIGN PATENT DOCUMENTS

EP    1184156 A1    3/2002
EP    2636511 A1    9/2013

OTHER PUBLICATIONS

Terrence O'Brien, "Mink will let you 3D print custom makeup at home", May 27, 2014; Retrieved from the Internet: URL:http://www.engadget.com/2014/05/07/mink-will-let-you-3d-print-custom-makeup-at-home/.

* cited by examiner

Primary Examiner — Leo B Tentoni
(74) Attorney, Agent, or Firm — Polsinelli PC

(57) ABSTRACT

The method comprises the following steps:
(a) supplying at least one cosmetic material and supplying at least one photoactivatable material;
(b) forming a layer (19) comprising on at least a first region of the layer (19), a photoactivatable material supplied in step (a);
(c) illuminating at least the first region of the layer (19) to activate the photoactivatable material;
(Continued)

(d) forming an additional layer (19) on at least a second region of the additional layer (19), a photoactivatable material supplied in step (a), (e) illuminating at least the second region of the additional layer (19) to activate the photoactivatable material;

(f) repeating steps (d) to (e) until the three-dimensional object is formed.

The cosmetic composition comprised in the three-dimensional object or forming the three-dimensional object being recoverable after the three-dimensional object is formed.

17 Claims, 2 Drawing Sheets

(51) Int. Cl.
| | |
|---|---|
| *B29C 64/112* | (2017.01) |
| *B29C 39/02* | (2006.01) |
| *B29C 64/124* | (2017.01) |
| *B29C 64/165* | (2017.01) |
| *B33Y 80/00* | (2015.01) |
| *B33Y 10/00* | (2015.01) |
| *B33Y 30/00* | (2015.01) |
| *A61K 8/85* | (2006.01) |
| *A61K 8/92* | (2006.01) |
| *A61Q 1/04* | (2006.01) |
| *A61Q 15/00* | (2006.01) |
| *B29L 31/00* | (2006.01) |
| *A45D 33/02* | (2006.01) |
| *A61K 8/02* | (2006.01) |

(52) U.S. Cl.
CPC .............. *A61Q 15/00* (2013.01); *B29C 39/025* (2013.01); *B29C 39/123* (2013.01); *B29C 64/124* (2017.08); *B29C 64/165* (2017.08); *B33Y 10/00* (2014.12); *B33Y 30/00* (2014.12); *B33Y 80/00* (2014.12); *A45D 33/02* (2013.01); *A61K 8/022* (2013.01); *B29L 2031/718* (2013.01)

(58) Field of Classification Search
CPC ... B29C 64/124; B29C 64/129; B29C 64/135; B29C 64/165
USPC ............... 264/255, 401, 460, 463, 494, 497
See application file for complete search history.

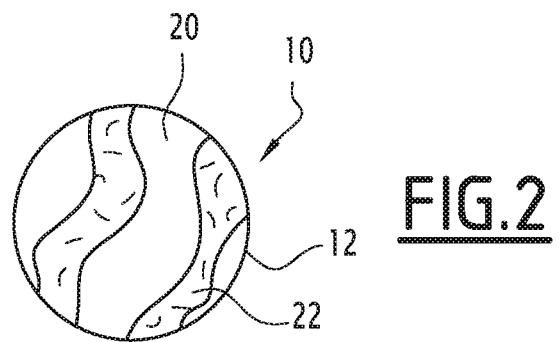
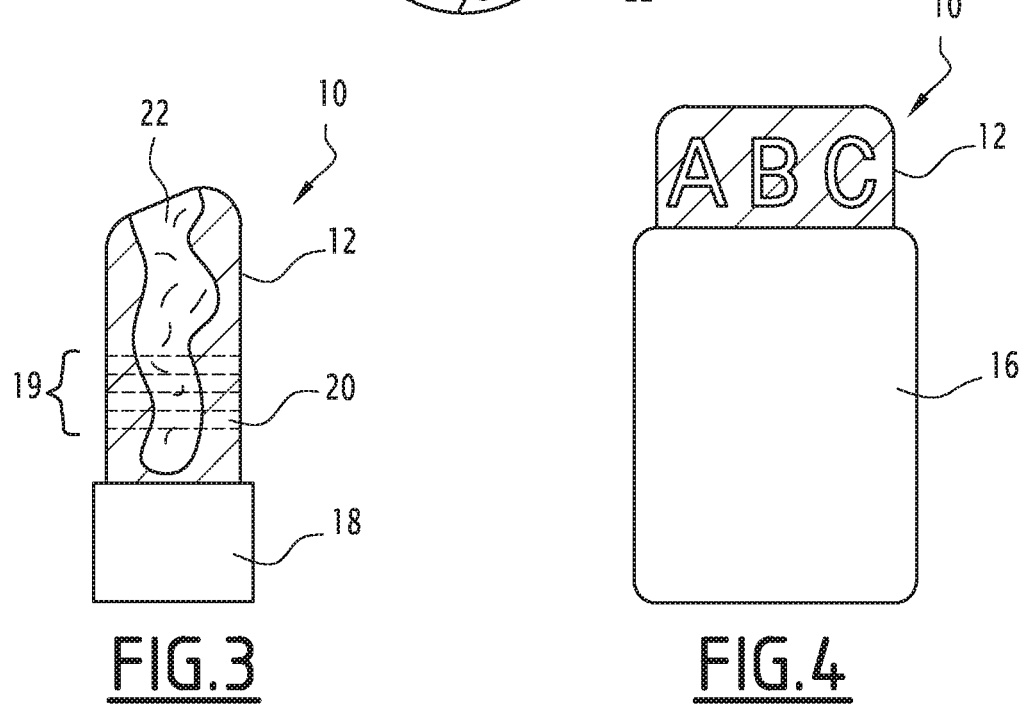

METHOD FOR THE ADDITIVE MANUFACTURE OF A THREE-DIMENSIONAL OBJECT COMPRISING OR FORMING A COSMETIC COMPOSITION BY DIRECT PROJECTION USING A PHOTOACTIVATABLE MATERIAL

CROSS REFERENCE TO RELATED APPLICATIONS

This application is a National Phase filing under 35 U.S.C. § 371 of PCT/EP2015/068062 filed on Aug. 5, 2015; and this application claims priority to Application No. 1457619 filed in France on Aug. 5, 2014 under 35 U.S.C. § 119. The entire contents of each application is hereby incorporated by reference.

This invention relates to a method for the manufacture of a three-dimensional object containing or forming a cosmetic composition The cosmetic composition contains at least one cosmetic product, in particular a makeup product, a care product, a washing product or a perfume, the cosmetic product being intended to be applied on a surface of the body of a user.

More generally, "cosmetic product" means in particular, in the sense of this invention, a product such as defined in Regulation (EC) no. 1223/2009 of the European Parliament and of the Council of Nov. 30, 2009 relating to cosmetic products.

According to the invention, the three-dimensional object advantageously forms a lipstick, a stick, a hybrid powder, a deodorant and/or antiperspirant product, a soap, a face mask, a hair styling wax, and/or a solid perfume.

In order to manufacture a three-dimensional object comprising a cosmetic composition, it is known to use methods for forming such as molding, filling, compaction, multi-compaction, wet powder injection, extrusion, etc.

Such methods for manufacture impose constraints on the objects manufactured. In molding, the objects generally have a cutting limit, with a maximum undercut possible when they are molded, even in a flexible mold.

The methods of molding also limit the complexity of the shapes, since it is impossible to create a part in another, or to nest one part in another.

In all of the aforementioned methods, the height of the product is a limiting factor. Complex shapes, in particular three-dimensional are very difficult, and even impossible to create, and often very expensive.

There are also limits in the coloring of the cosmetic composition, in particular in the number of colors that can be used, and in the control of the various colors in the cast mass. It is in particular tedious to create objects that have different colors and/or color shading, and/or graphic inscriptions, for example alphanumeric characters and/or juxtapositions of colors.

The aforementioned methods are also limited in the implementation of different precursor materials in order to form the cosmetic composition. It is for example tedious to create via the same method an object formed of cosmetic products of different natures and compositions.

Another difficulty results from the fact that the method of the aforementioned type are intended solely for the formation of the three-dimensional object.

In certain cases, it is necessary to prepare upstream of the formation at least one bulk, which complicates the manufacture in certain cases.

Moreover, when new objects integrating cosmetic compositions are developed, it is generally useful to create working models making it possible to determine the feasibility and the interest of the object.

These models are complex to create, and require many steps comprising the development of the formula, the manufacture of the bulk, the creating of a special tool, and product packaging or formation tests.

These tests sometimes have to be conducted several times before a satisfactory result is obtained, which increases development time and costs.

One aim of the invention is to provide a simple and versatile method for manufacturing three-dimensional objects comprising a cosmetic composition, with the objects able to have complex shapes, natures and appearances.

For this purpose, the invention relates to a method of the aforementioned type, comprising the following steps:

(a) supplying at least one cosmetic material and supplying at least one photoactivatable material;

(b) forming a layer comprising one or a plurality of cosmetic materials supplied in step (a) and on at least a first region of the layer, a photoactivatable material supplied in step (a);

(c) illuminating at least the first region of the layer to activate the photoactivatable material;

(d) forming an additional layer comprising one or a plurality of cosmetic materials supplied in step (a) and, on at least a second region of the additional layer, a photoactivatable material supplied in step (a), the additional layer at least partially covering the previous layer;

(e) illuminating at least the second region of the additional layer to activate the photoactivatable material;

(f) repeating steps (d) to (e) until the three-dimensional object is formed, the cosmetic composition comprised in the three-dimensional object or forming the three-dimensional object being recoverable after the three-dimensional object is formed.

The method according to the invention can include one or more of the following features, taken alone or in any technically possible combination:

- the photoactivatable material comprises a photoinitiator and a photocrosslinkable compound capable of being activated by the photoinitiator.
- the photocrosslinkable compound comprises at least one monomer, and/or at least one prepolymer and/or at least one polymer, particularly chosen from polyesters with unsaturation(s) or (meth)acrylate groups, polyurethanes and/or polyureas with (meth)acrylate groups, polyethers with (meth)acrylate groups, epoxyacrylates, polyorganosiloxanes with (meth)acrylate or (meth)acrylamide groups, perfluoropolyethers with acrylate groups, a polyene associated with a polythiol, the mixtures thereof or copolymers thereof.
- the photoactivatable material is deposited in liquid form via a nozzle on the first region and/or on the second region.
- depositing the photoactivatable material comprises positioning the nozzle in a succession of given positions on the first region and/or on the second region, and, in each given position, depositing a given quantity of photoactivatable material, illuminating the photoactivatable material deposited in the given position, and moving the nozzle to another given position on the first region and/or on the second region.
- a first cosmetic material supplied in step (a) has a first color, a second cosmetic material supplied in step (a) having a second color, the cosmetic composition formed comprising first cosmetic material and second cosmetic material on the same layer or on different layers.

the photoactivatable material is included in or forms a cosmetic material intended to be deposited in liquid form.

at least one layer comprises a photoactivatable substrate material suitable for forming a substrate of the cosmetic composition, the substrate being non-recoverable, the method comprising illuminating the photoactivatable substrate material to form at least a part of the substrate.

in step (a), at least one cosmetic material contains at least one structuring agent in liquid form, the method comprising a preliminary step for heating the cosmetic material(s) supplied in step (a) in order to melt the or each structuring agent;

each layer formed in step (b) comprising one or a plurality of heated cosmetic materials, the or each structuring agent contained in the cosmetic material(s) being deposited in the molten state;

the layer being at least partially solidified by cooling the or each cosmetic material to a temperature below that of the or each cosmetic material deposited in step (b);

each additional layer formed in step (d) comprising one or a plurality of heated cosmetic materials, the or each structuring agent contained in the cosmetic material(s) being deposited in the molten state;

the additional layer being at least partially solidified by cooling the or each cosmetic material to a temperature below that of the or each cosmetic material deposited in step (c);

the photoactivatable material being deposited in at least one at least partially liquid layer.

the heating temperature of the or each cosmetic material in step (a) is greater than 50° C. and is advantageously between 60° C. and 110° C.;

the depositing temperature of the or each cosmetic material in step (b) and in step (d) is less than or equal to the heating temperature, advantageously greater than the solidification temperature of the or each cosmetic material plus 5° C.

the cooling of the or each cosmetic material in step (b) and in step (d) is greater than 3° C., advantageously greater than 5° C.;

the structuring agent is chosen from waxes, organophilic clays, pyrogenic silicas, fatty acids, pasty compounds, gelling agents, thickening agents, glutamide resins, hydrophobic celluloses, tackifying resins, and mixtures thereof.

the precursor material of the cosmetic composition comprises a mass wax content greater than 10%.

the three-dimensional object is a lipstick, a stick, a hybrid powder, a deodorant and/or antiperspirant product, a soap, a face mask, a hair styling wax, and/or a solid perfume.

The invention also relates to an apparatus for the additive manufacture of a three-dimensional object comprising or forming a cosmetic composition, the apparatus comprising:
a substrate surface;
an assembly for forming successive layers comprising at least one cosmetic material and for at least one layer, a photoactivatable material;
a source for illuminating the photoactivatable material;
a control unit, suitable for controlling the formation assembly, and the illumination source to perform the following steps:
(a) supplying at least one cosmetic material and supplying at least one photoactivatable material;
(b) forming a layer comprising one or a plurality of cosmetic materials supplied in step (a) and on at least a first region of the layer, a photoactivatable material supplied in step (a);
(c) illuminating at least the first region of the layer to activate the photoactivatable material;
(d) forming an additional layer comprising one or a plurality of cosmetic materials supplied in step (a) and, on at least a second region of the additional layer, a photoactivatable material supplied in step (a), the additional layer at least partially covering the previous layer;
(e) illuminating at least the second region of the additional layer to activate the photoactivatable material;
(f) repeating steps (d) to (e) until the three-dimensional object is formed, the cosmetic composition comprised in the three-dimensional object or forming the three-dimensional object being recoverable after the three-dimensional object is formed.

The device according to the invention can include one or more of the following features, taken alone or in any technically possible combination:
the light source is chosen from a lamp and a laser.
the assembly comprises at least one nozzle for dispensing each cosmetic material, the light source being suitable for moving in conjunction with the nozzle.

The invention will be easier to understand in view of the following description, provided solely as an example, and with reference to the appended drawings, wherein:

FIGS. 2 to 4 show examples of three-dimensional objects created by a method according to the invention, using the apparatus of FIG. 1;

Figure 1:
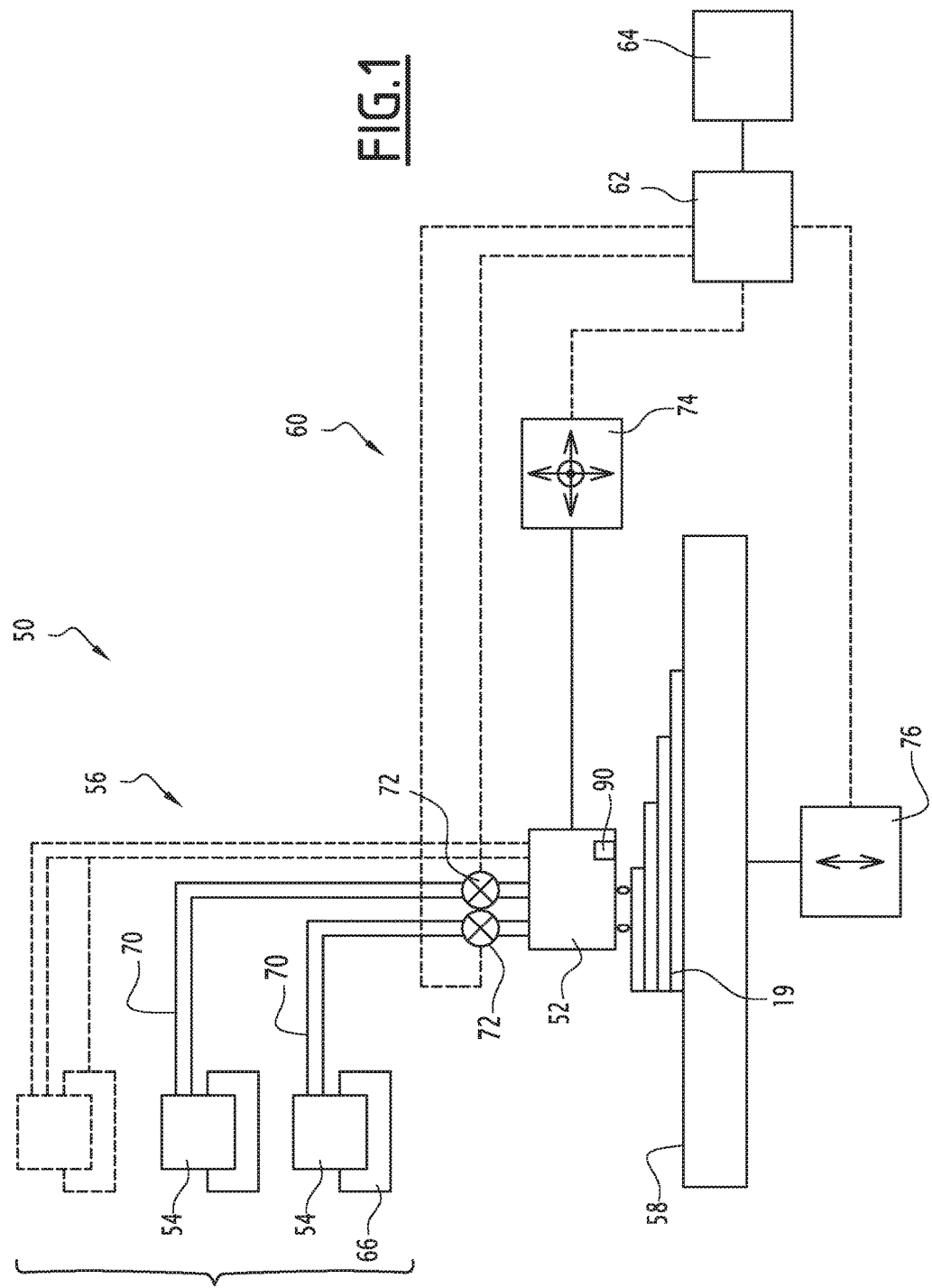
FIG. 1 is a diagrammatic view of an example of an apparatus, intended for the manufacture of a three-dimensional object comprising a cosmetic composition, by a method according to the invention.

This invention relates to a method for manufacturing three-dimensional objects 10 comprising a cosmetic composition 12 or formed from a cosmetic composition 12, using an apparatus for additive deposit manufacturing in liquid form of layers, of which an example is shown in FIG. 1.

The method according to the invention is intended to manufacture three-dimensional objects 10 formed of a cosmetic composition 12, such as shown for example in FIG. 2 to be provided directly to the user or to be inserted into a separately manufactured packaging 16 of the cosmetic composition 12 such as shown in FIG. 4.

In an alternative, shown in FIG. 3, the method according to the invention is also intended to manufacture by additive deposit three-dimensional objects 10 comprising, in addition to the cosmetic composition 12, a substrate 18 bearing the cosmetic composition 12, the substrate 18 being manufactured simultaneously by additive deposit with the cosmetic composition 12.

According to the invention, the cosmetic composition 12, and if applicable the substrate 18, are formed of a plurality of successive layers 19 formed using at least one photoactivatable material, deposited on each other.

The successive layers 19 are deposited in liquid form, and solidify at least under the effect of light radiation, the photoactivatable material forming a cosmetic material included in the layer 19 in liquid form or forming the layer 19 in liquid form.

The photoactivatable material is therefore included in or forms a cosmetic material. Alternatively, the photoactivatable material is therefore included in or forms a photoactivatable binder intended to bind at least one cosmetic material, in particular a powder.

Advantageously, the photoactivatable material comprises at least one photoinitiator and at least one photocrosslinkable compound capable of being activated by the photoinitiator.

The photocrosslinkable compound generally comprises one or a plurality of polymers and/or prepolymers comprising double ethylene-polymerisable bonds, and/or one or a plurality of double bond reactive monomers.

Double bond reactive monomers, when they are present, are generally one or a plurality of vinyl monomers, for example acrylates or methacrylate, in particular acrylic or methacrylic acid esters.

Each reactive monomer comprises at least one double ethylene bond, and preferably several double ethylene bonds.

The polymer or polymers and/or prepolymers comprising double ethylene bonds have an average number of double ethylene bonds per polymer molecule greater than 1.

As examples of photocrosslinkable polymers and prepolymers that can be used in the photocrosslinkable compound, mention may be made of:
- polyesters with unsaturation(s); this is a group of polymers of the polyester type that has one or a plurality of double ethylene bonds, distributed at random in the main chain of the polymer.
- polyesters with lateral and/or terminal (meth)groups obtained by means of polycondensation of a mixture of linear or branched or cycloaliphatic aliphatic dicarboxylic acids, of linear or branched or cycloaliphatic aliphatic diols;
- polyurethanes and/or polyureas with (meth)acrylate groups, obtained by means of polycondensation of cycloaliphatic and/or aromatic aliphatic diisocyanates, triisocyanates and/or polyisocyanates, of at least one (meth)acrylic acid ester et of one diol or polyol, of polyols, in particular of diols, free from ethylene-polymerisable unsaturations, and of at least one (meth)acrylic acid ester and of a diol or polyol;
- polyethers with (meth)acrylate groups obtained by means of esterification, by (meth)acrylic acid, terminal hydroxyl groups of homopolymers or of copolymers of C1-4 alkylene glycols;
- epoxyacrylates obtained by means of a reaction between at least one diepoxide and one or a plurality of carboxylic acids or carboxylic polyacids comprising at least one double ethylene bond;
- polyorganosiloxanes with (meth)acrylate or (meth)acrylamide groups obtained respectively by means of esterification, advantageously by (meth)acrylic acid, polyorganosiloxanes, and by amidification, for example by (meth)acrylic acid, of polyorganosiloxanes carrying lateral and/or terminal primary or secondary amine groups;
- perfluoropolyethers with acrylate groups obtained by means of esterification, for example by (meth)acrylic acid, of perfluoropolyethers carrying lateral and/or terminal hydroxyl groups;
- a polyene such as defined hereinabove associated with a polythiol;
- mixtures or copolymers thereof.

The photoinitiator or photoinitiators that can be used in the photoactivatable material of this invention are described, for example in the following articles of which the content is an integral part of this application: "Les photoiniateurs dans la réticulation des revêtements", G. Li Bassi, Double Liaison—Chimie des Peintures, No. 361, November 1985, pages 34-41; industrielles de la polymerisation photoinduite", Henri Strub, L'Actualité Chimique, February 2000, pages 5-13; and "Photopolymères: théoriques et réaction de prise", Marc, J. M. Abadie, Double Liaison—Chimie des Peintures, No. 435-436, 1992, pages 28-34.

These photoinitiators include the alpha-hydroxyketones, alpha-aminoketones, chloroacetophenones, aromatic ketones, thioxanthones and quinones, benzoin ethers, acylphosphine oxides, and copolymerizable photoinitiators.

Copolymerizable photoinitiators are molecules comprising both a photoinitiator group capable of photoinduced radical splitting and at least one double ethylene bond.

According to the first aspect of the invention, the photoactivatable material is included in at least one cosmetic material capable of being deposited in liquid form and of at least partially solidifying by crosslinking under the effect of a radiation and/or of heat.

Alternatively, the photoactivatable material forms a cosmetic material as such, intended to partially form the cosmetic material. In the latter case, at least one other cosmetic material is capable of being deposited in liquid form with the photoactivatable material and of at least partially solidifying by cooling.

The radiation suitable for the crosslinking of the cosmetic compositions according to the present invention has a wavelength between 210 nm and 600 nm, preferably between 250 nm and 400 nm.

In one preferred embodiment of the invention, a UV lamp and particularly a mercury vapor lamp, optionally doped with further elements, such as gallium, suitable for modifying the emission spectrum of the light source, is used. Alternatively or in addition, a laser is used to cause the crosslinking.

Advantageously, several different cosmetic materials are used to form the cosmetic composition, by being deposited within the same layer or in different layers.

The different cosmetic materials have for example different compositions, in order to form, within the cosmetic composition 12, regions 20, 22 with a different composition and/or appearance, for example in terms of chemical nature, mechanical properties and/or colors, as shown for example in FIG. 2 or 3, or shadings of composition and of color. In particular, different cosmetic materials have different colors.

In one example, all of the layers 19 are created using the same cosmetic material. Alternatively, a layer 19 is created using a first cosmetic material, and at least one additional layer 19 created using a second cosmetic material different from the first cosmetic materials.

Also alternatively, at least one layer 19 is created using the first cosmetic material, and partially using the second cosmetic material different from the first cosmetic material.

The thickness of each layer 19 forming the three-dimensional object 10 is for example less than 50 μm and is in particular between 10 μm and 30 μm.

Each layer 19 comprises at least one filled area formed of at least one cosmetic material. Optionally, each layer 19 comprises empty areas defined by adjacent filled areas, according to the desired shape of the three-dimensional object 10.

Each layer 19 comprises at least one filled area formed of at least one cosmetic material. Optionally, each layer 19 comprises empty areas defined by adjacent filled areas, according to the desired shape of the three-dimensional object 10.

At ambient temperature, for example at 25° C., the cosmetic composition is structured. "Structured" means in particular, in the sense of this invention, that the cosmetic composition has its own mechanical resistance, i.e. it spontaneously retains its shape, throughout the entire lifetime of the product in the absence of external stress. This lifetime is for example at least one day, and in particular at least one year.

As such, the cosmetic composition in the three-dimensional object formed at the end of the method according to the invention is not liquid at ambient temperature, and does not spontaneously flow in a macroscopically visibly manner for at least one minute and advantageously, for at least one day, in the absence of external stress.

Preferably, the cosmetic composition is solid. In this case, it can be grasped and moved by the user, without flowing.

According to the invention, the cosmetic composition is recoverable. "Recoverable" means in particular, in the sense of this invention, that at least a portion of the cosmetic composition can be applied on a body surface of the user and that the composition is capable of being at least partially detached from the three-dimensional object in order to remain on the body surface.

In particular, the crosslinking supplied by the photoactivatable material is not total and does not prevent the cosmetic material from being recoverable.

Advantageously, the cosmetic composition is recoverable by friction between the body surface and the cosmetic composition, without physical deterioration of the body surface. Alternatively, the cosmetic composition is recoverable by friction between an applicator and the cosmetic composition.

In one alternative, the cosmetic composition is recoverable by soaking in a biologically compatible liquid in order to at least partially detach it from the three-dimensional object and apply it on the body surface.

In one alternative, the cosmetic composition can be restored by prior heating of the three-dimensional object at a biologically compatible temperature, for example less than 60° C.

Advantageously, the cosmetic composition is chosen from a colored cosmetic composition, and in particular a makeup composition for the skin and/or mucosa.

In particular such a composition can be a foundation, a blush, a powder, a blusher or eye shadow, an anti-wrinkle compound, a lipstick or a lip gloss, a transparent or non-transparent stick, a block of deodorant and/or of antiperspirant, a soap, a transparent soap, a face mask, a hair styling wax, a solid perfume, optionally having care or treatment properties.

This can be a colored makeup composition intended to correct the color of the foundation.

A composition according to the invention can also form a makeup composition or nail or eyelash care.

A composition according to the invention can also have the form of an anhydrous gel, oil-in-water or water-in-oil emulsion or dispersion or in the form of a multiple emulsion. It can have the form of a paste, more or less rigid solid, cream, ointment. It can be of anhydrous form, and more especially in the form an an anhydrous gel, in particular cast as a stick or dish.

The or each cosmetic material is intended to be heated in order to be deposited in at least partially liquid form under heat into a layer, then to be at least partially solidified by cooling and/or by crosslinking, after its depositing in a layer.

By "at least partially liquid" we generally mean that the cosmetic material is able to flow under the effect of its own weight. In particular, the cosmetic material is able to flow through an extrusion nozzle or extrusion head.

The "at least partially liquid" material is entirely liquid, or comprises a liquid phase in which are dispersed solid elements, which flow by the intermediary of the liquid phase.

In particular, the cosmetic material is at least partially liquid due to the melting of the or of each structuring agent contained in the cosmetic material.

"Under heat" means in particular above the melting point of the or of each structuring agent, such as measured by ISO standard 11357-3: 2011.

Advantageously, each material is deposited in the form of droplets of liquid under heat which are sprayed using a nozzle onto a substrate, or onto a previous layer of the three-dimensional object being formed.

The at least partially liquid cosmetic material is able to at least partially solidify by cooling and/or by crosslinking. By "at least partially solidify" we mean that the cosmetic material is able to be structured, in the sense defined hereinabove. In particular, the viscosity of the material is able to increase. In particular, the material is able to become solid.

The cooling advantageously changes each structuring agent contained in the cosmetic material to a temperature less than the temperature that it had when it was deposited. This temperature is preferably less than the melting point of the cosmetic material.

The temperature loss of the cosmetic material during cooling is greater than 3° C., in particular greater than 5° C.

In order to ensure the structuring of the cosmetic material and form the cosmetic composition, each cosmetic material comprises at least one structuring agent.

In one example, each cosmetic material comprises a first structuring agent that is common to all the cosmetic materials.

Alternatively, a first cosmetic material comprises a first structuring agent, and a second cosmetic material different from the first cosmetic material comprises a second structuring agent different from the first structuring agent.

The structuring agent is able to melt at a temperature greater than its melting point in order to allow for the depositing in liquid form of the cosmetic material in a layer. It is able to solidify by cooling to a temperature less than its melting point after the depositing into a layer.

The term structuring agent denotes a compound able to increase the viscosity of the composition incorporating it. The structuring agent makes it possible in particular to obtain a composition that can have a texture ranging from fluid to solid textures.

In order to ensure an adequate deposit, the melting point of the cosmetic composition containing the or each structuring agent is for example grater than 50° C. and is advantageously between 60° C. and 110° C. For the purpose of the invention, the melting point corresponds to the temperature of the most endothermic peak observed in thermal analysis (DSC) as described in ISO standard 11357-3: 2011.

Those skilled in the art will know how to choose the adequate protocol according to the composition for which it is desired to measure to the melting point.

In particular, the melting point of the composition can be measured using a differential scanning calorimeter (DSC), for example the calorimeter sold under the trade name "MDSC 2920" by TA Instruments. The measurement protocol is as follows:

A 5 mg sample of the composition placed in a crucible is subjected to a first temperature rise from −20° C. to 100° C., at a heating rate of 10° C./minute, and then is cooled from 100° C. to −20° C. at a cooling rate of 10° C./minute and finally subjected to a second temperature rise from −20° C. to 100° C. at a heating rate of 5° C./minute. During the second temperature rise, the variation in the difference in power absorbed by the empty crucible and by the crucible containing the composition sample as a function of temperature is measured. The melting point of the compound is the value of the temperature equivalent to the top point of the peak of the curve representing the variation in the difference in power absorbed as a function of temperature.

On the other hand, the solidification point is the value of the temperature equivalent to the top point of the peak of the curve representing the variation in the difference in power absorbed as a function of temperature during the falling in temperature following the second temperature rise.

The softening point of the cosmetic composition containing the or each structuring agent is for example between 50° C. and 70° C. This softening point is measured according to the protocol described in standard NF T66-147.

The density of the cosmetic composition containing the or each structuring agent, taken at its melting point according to the standard ASTM D4164, is for example between 0.7 and 1, in particular between 0.8 and 0.9.

The volumetric shrinkage of the cosmetic composition containing the or each structuring agent, measured at 40° C. at ambient temperature, for example 25° C., is less than 3%, and is in particular between 1.5% and 2.5%. This volumetric shrinkage is measures according to the protocol described in standard NF EN ISO 294-4, May 2003.

The or each structuring agent in each cosmetic material contained in the cosmetic composition, forms a network for maintaining the composition. This network breaks on the surface during the application of the cosmetic product, allowing for the restoration of the composition.

A structuring agent or mixture of structuring agents may be present in the composition at a content ranging from 4% to 40% by weight, in relation to the total weight of the composition, preferably ranging from 4% to 30% by weight.

The structuring agent according to the invention is chosen for example from:
  waxes,
  organophilic clays,
  pyrogenic silicas,
  fatty acids,
  pasty compounds;
  gelling agents, particularly organogelators;
  thickening agents;
  glutamide resins;
  hydrophobic celluloses,
  tackifying resins, and
  mixtures thereof.

A wax, in the sense of this invention, is a lipophilic fat compound, solid at ambient temperature (25° C.), having a reversible solid/liquid change of state, having a melting point greater than about 45° C. (measured by DSC) and better greater than 50° C. and up to 95° C., and having in the solid state, an anisotropic crystalline organization. The waxes suitable for the invention may be hydrocarbon, silicone and/or fluorinated compounds, optionally comprising ester or hydroxyl functions.

As waxes that can be used in the composition of the invention, mentioned may be made for example of mineral waxes such as microcrystalline waxes, paraffin, Vaseline, ozokerine, montan wax; waxes of animal origin such as beeswax, shellac wax, lanolin and the derivatives thereof; waxes of plant origin such as Candellila wax, Ouricury wax, Carnauba wax; Sunflower wax, Japanese rice bran, cocoa butter, cork fiber wax or sugarcane wax; hydrogenated oils solid at 25° C.; fatty esters and glycerides solid at 25° C.; synthetic waxes such as polyethylene waxes and waxes obtained by Fisher-Tropsch synthesis; silicone waxes, and mixtures thereof, glucoside waxes.

Mention may also be made of waxes obtained by means of the catalytic hydrogenation of animal or plant oils having C8-C32 linear or branched fat chains. Mention may also be made of silicone waxes, fluorinated waxes, waxes obtained by hydrogenating esterified castor oil with cetyl alcohol.

As fatty acid, mention may be made of fatty acids, having a fatty chain comprising from 8 to 28 carbon atoms, with the number of ethylene oxide and propylene oxide groups able to range from 2 to 50 and that of glycerol in particular from 2 to 30. As a gelling agent, mention may be made of glyceryl alginates, propylene glycol alginates, gellan gum and welan gum.

For the purposes of the invention, the term "pasty compound" refers to a lipophilic fat compound having a reversible solid/liquid change of state, having in the solid state, an anisotropic crystalline organization, and comprising at a temperature of 23° C. a liquid fraction and a solid fraction. The pasty compound is preferably chosen from synthetic compounds and plant-based compounds. A pasty compound may be obtained by means of synthesis from plant-based starting materials.

The pasty compound can be advantageously chosen from:
  lanolin and the derivatives thereof,
  optionally polymeric silicone compounds,
  optionally polymeric fluorinated compounds,
  vinyl polymers, in particular:
  olefin homopolymers,
  olefin copolymers,
  hydrogenated diene homopolymers and copolymers
  linear or branched oligomers, alkyl (meth)acrylate homo or copolymers preferably having a C8-C30 alkyl group,
  vinyl ester homo and copolymer oligomers, having C8-C30 alkyl groups, and
  vinyl ester homo and copolymer oligomers, having C8-C30 alkyl groups
  liposoluble polyethers derived from polyetherification between one or a plurality of C2-C100, preferably C2-C50, diols,
  esters
  mixtures thereof.

As gelling agents, mention may be made of lipophilic, mineral and organic gelling agents.

As thickening agent, mention may be made of carboxyvinyl polymers, polyacrylamides, 2-acrylamido-2-methylpropanesulfonic acid polymers and copolymers, optionally crosslinked and/or neutralized, 2-acrylamido 2-methylpropane sulfonic acid and hydroxyethyl acrylate copolymers, cellulosic derivatives; polysaccharides and in particular gums such as Xanthan gum, hydroxypropyl guar gums; silicas.

The thickening agent can also be cationic.

"Glutamide resin" means, in the sense of this invention, a N,N'-dialkyl acylglutamide.

The term tackifying resin denotes a resin having a mean molecular weight by number less than or equal to 10,000 g/mol, in particular ranging from 250 to 10,000 g/mol preferably less than or equal to 5,000 g/mol, in particular ranging from 250 to 5,000 g/mol, better, less than or equal to 2,000 g/mol in particular ranging from 250 to 2,000 g/mol and even better less than or equal to 1,000 g/mol in particular ranging from 250 to 1,000 g/mol.

Mean molecular weights by number (Mn) are determined by gel permeation liquid chromatography (solvent THF, calibration curve established with polystyrene calibration standards, refractometric detector).

The resin of the composition according to the invention is advantageously a so-called tackifying resin. Such resins are in particular described in the Handbook of Pressure Sensitive Adhesive, edited by Donatas Satas, 3rd ed., 1989, p. 609-619.

The resin of the composition according to the invention is chosen from colophony, colophony derivatives, hydrocarbon resins and mixtures thereof, and preferably from hydrocarbon resins.

Colophony is a mixture mainly comprising organic acids called colophony acids (mainly acids of the abietic type and of the pimaric type).

There are three types of colophony: colophony ("gum rosin") obtained by incision in live trees, wood rosin, which is extracted from stumps or from pine wood, and tall oil rosin, which is obtained from a by-product coming from the production of paper.

Colophony derivatives can come in particular from polymerization, hydrogenation and/or esterification (for example with polyhydric alcohols such as ethylene glycol, glycerol, pentaerythritol) of colphony acids. Hydrocarbon resins are chosen from polymers of low molecular weight which can be categorized, according to the type of monomer that they contain, as:

indenic hydrocarbon resins.
 pentanediene aliphatic resins
 pentanediene and indene mixed resins
 diene resins of dimers of cyclopentanediene
 diene resins of dimers of isoprene
 hydrogenated C6-C20 polyolefins.

The resin can be chosen from indenic hydrocarbon resins, preferably hydrogenated. Preferably, the indenic hydrocarbon resin comes from the polymerization of indene monomer and from monomer chosen from styrene, methylindene, methylstyrene and mixtures thereof.

Advantageously, the cosmetic material comprises a mass wax content greater than 10%, and in particular between 10% and 30%, particularly between 15% and 20%.

Advantageously, the structuring agent comprises at least one wax, and preferably a mixture of waxes Preferably, the mixture of waxes comprises a first wax having a melting point greater than 80° C., at least one second wax having a melting point between 60° C. and 80° C., and at least one third wax having a melting point between 50° C. and 60° C.

The first mass wax content in the cosmetic material is for example between 6% and 10%, in particular between 7% and 8%.

The second mass wax content is for example between 2% and 5%, in particular between 3% and 4%.

The third mass wax content is for in particular between 2% and 7%, for example between 3% and 5%.

The cosmetic material comprises in addition to the structuring agent ingredients that are compatible with the skin, lips and skin appendages such as keratin fibers.

Advantageously, the cosmetic material comprises in addition to the structuring agent, an additional agent chosen for example from oils, pastes, coloring agents, fillers, surfactants, sequestrants, neutralizing agents, antioxidants, softeners, opacifiers, stabilizers, colorants, perfumes, cosmetic active substances, reducing agents, essential oils, preservatives, bactericides, hydrating agents, vitamins, essential fatty acids, sphingolipids, self-tanning agents as for example DHA, sun filters, antifoam agents, sequestering agents, thickening or suspension agents, any other ingredient routinely used in cosmetics.

A coloring agent may be chosen from water-soluble or liposoluble colorants, pigments, nacres and mixtures thereof. The composition according to the invention can further comprise one or a plurality of dyes chosen from water-soluble colorants, and powder dyes such as pigments, nacres and glitter well know to those skilled in the art.

The pigments are for example mineral pigments such as metal oxides, in particular iron and titanium of organic pigments.

The term "nacres" should be understood to mean iridescent or non-iridescent colored particles of any shape, which are in particular produced by certain mollusks in their shell or else are synthesized and which exhibit a color effect by optical interference.

The nacres may be selected from pearlescent pigments such as titanium mica coated with iron oxide, titanium mica coated with bismuth oxychloride, titanium mica coated with chromium oxide, titanium mica coated with an organic dye, and pearlescent pigments based on bismuth oxychloride. This may also involve mica particles at the surface whereof are superposed at least two successive layers of metal oxides and/or of organic dyes.

By way of example of nacres, mention may also be made of natural mica coated with titanium oxide, with iron oxide, with natural pigment or with bismuth oxychloride.

The nacres may more particularly possess a yellow, pink, red, bronze, orange, brown, gold and/or copper color or glint.

The term "colorants" refers to generally organic compounds soluble in fats such as oils or in a hydroalcoholic phase.

The liposoluble colorants can be chosen from Sudan Red, DC Red 17, DC Green 6, β-carotene, Sudan Brown, DC Yellow 11, DC Violet 2, DC orange 5 and Quinoline Yellow. The water-soluble colorants are, for example, beetroot juice and methylene blue.

The cosmetic composition according to the invention may also contain at least one material with a specific optical effect.

This effect is different from a simple conventional hue effect, i.e. a unified and stabilized effect of the kind produced by conventional dyes, such as, for example, monochromatic pigments. For the purpose of the invention, the term "stabilized" signifies absence of an effect of variability of color with the angle of observation or in response to a temperature change.

For example, this material may be selected from particles having a metallic glint, goniochromatic coloring agents, diffracting pigments, thermochromatic agents, optical brighteners, and also fibers, in particular of the interference type. Of course, these various materials may be combined so as to provide the simultaneous manifestation of two effects.

The metallic-glint particles that can be used in the invention are in particular chosen from: —particles of at least one metal and/or of at least one metal derivative, particles comprising a single-substance or multi-substance, organic or mineral substrate, at least partially coated with at least one metallic-glint layer comprising at least one metal and/or at least one metal derivative, and mixtures of said particles. Among the metals that may be present in said particles, mention may, for example, be made of Ag, Au, Cu, Al, Ni, Sn, Mg, Cr, Mo, Ti, Zr, Pt, Va, Rb, W, Zn, Ge, Te, Se and mixtures or alloys thereof. Ag, Au, Cu, Al, Zn, Ni, Mo, Cr and mixtures or alloys thereof (for example, bronzes and brasses) are preferred metals.

The term "metal derivatives" denotes compounds derived from metals, in particular oxides, fluorides, chlorides and sulfides.

A composition according to the invention may comprise at least one filler.

The term "fillers" should be understood for the purposes of the invention to denote inorganic or synthetic colorless or white particles of any shape, insoluble in the medium of the composition regardless of the temperature at which the composition is manufactured. These fillers may particularly be used to modify the rheology or texture of the composition.

The fillers may be mineral or organic particles of any shape, in sheet, spherical or oblong form, regardless of the crystallographic shape (for example sheet, cubic, hexagonal, orthorhombic, etc). Mention may be made of talc, mica, silica, clays such as bentonite, kaolin, polyamide, poly-β-alanine and polyethylene powders, tetrafluoroethylene polymer powders, lauroyl-lysine, starch, boron nitride, polymeric hollow microspheres such as those of polyvinylidene chloride/acrylonitrile of acrylic acid copolymers and silicone resin microbeads, elastomer polyorganosiloxane particles, precipitated calcium carbonate, magnesium carbonate and hydro-carbonate, hydroxyapatite, hollow silica microspheres, glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate.

This can also be particles containing a copolymer, said copolymer comprising trimethylol hexyllactone. In particular, it may be a copolymer of hexamethylene diisocyanate/trimethylol hexyllactone.

As indicated hereinabove, in one alternative, the cosmetic composition is a lipstick. Lipsticks can, according to prior art, have two forms: in the form of a stick or in the form of a flexible paste. In this case, the cosmetic material contains at least one wax in a fatty phase.

A conventional form combines about 7 to 8 wt % hard wax (melting point greater than 80° C.), 3 to 4 wt % intermediate wax (melting point between 60 and 80° C.), and 3 to 5 wt % soft wax (melting point between 50 and 60° C.).

For the pasty types, there are two types, the solid crystalline type at ambient temperature, characterized by a melting point between 30 and 50° C., and the pasty type with a flexible paste.

Lipsticks can comprise oils. "Oil" means a liquid fatty body at ambient temperature (25° C.) and atmospheric pressure (760 mm Hg namely $1.05 \times 10^5$ Pa). The oil may be chosen from any physiologically acceptable and particularly cosmetically acceptable oils, in particular mineral, animal, plant, synthetic oils; in particular, volatile or non-volatile hydrocarbon and/or silicone and/or fluorinated oils and mixtures thereof.

Oil can comprise a gelling agent, such as a polymer, in particular a modified sugar. For the preparation of lipstick, the cosmetic material can comprise at least one polymeric system which comprises at least one film-forming polymer. Film-forming polymers include synthetic polymers of the radical type obtained from the copolymerization of $C_1$-$C_8$ alkyl methacrylate monomers, optionally combined with acrylic acid, syrene and α-methyl styrene. "Radical polymer" means a polymer obtained by polymerization of monomers with unsaturation in particular ethylene monomers, with each monomer able to be homopolymerized (unlike polycondensates). Polymers of the radical type can be in particular vinyl polymers, or copolymers, in particular acrylic polymers.

Alkyl (meth)acrylates include methyl methacrylate, ethyl methacrylate, butyl methacrylate, isobutyl methacrylate, 2-ethyl hexyl methacrylate.

According to this invention, the ester alkyl group can either be fluorinated or be perfluorinated, i.e. a portion or all of the hydrogen atoms of the alkyl group are substituted with flourine atoms.

According to the invention, as a film-forming polymer a copolymer is preferably used chosen from acrylic/methacrylate acid copolymers, acrylic/methacrylate/styrene acid, as well as (meth)acrylate copolymers.

When the polymer used according to the invention comprises monomers carrying a salt-forming group (for example a carboxylic acid group), it can be neutralized, entirely or partially using a neutralizing agent (here a base for neutralizing the acid group) that is well known to those skilled in the art. The neutralization can furthermore favor the dispersion, in particular in water, of the polymer, and even stabilize said dispersion.

Advantageously, the radical film-forming polymer of the polymeric system is present in the composition according to the invention either in solubilized form (dissolved), or in dispersed form, i.e. is the form of a dispersion of particles, in particular in a cosmetically or dermatologically acceptable medium. Preferably, the radical film-forming polymer has the form of an aqueous dispersion of particles of said polymer.

For the preparation of lipstick, the cosmetic material can comprise at least one plasticizer and/or coalescing agent. In particular, mention can be made of, alone or in a mixture, standard plasticizer or coalescing agents, such as:
glycols and derivatives thereof;
glycerol esters,
propylene glycol derivatives,
esters of acids in particular carboxylic acids,
oxyethylenated derivatives,
water-soluble polymers that have a low glass transition temperature, less than 25° C., preferably less than 15° C.

Lipstick compositions also comprise fillers, pigment or nacre as defined hereinabove.

In another alternative, the cosmetic composition is a stick, in particular an aqueous or alcoholic stick, or a dry stick and/or an anhydrous cream.

A cosmetic composition in the form of a stick or cake can advantageously comprise a gel containing a compound chosen from the group consisting of: polyols, dibenzylideneoses, hardening agents, such as those of the sulfosuccinate type, and any of the mixtures thereof.

Compositions in the form of a solid stick or cake can comprise a mixture of various anhydrous and/or lipophilic constituents such as waxes (natural, plant, mineral or synthetic), oils (plant or mineral) and other fatty bodies (liquid fatty esters, synthetic triglycerides and solid fatty esters).

Compositions in the form of a solid stick or cake can be aqueous and comprise an active ingredient dissolved in a water/polyol phase gelled by a gelling agent, such as for example dibenzylidene sorbitol.

Compositions in the form of a solid stick or cake can be transparent.

Of the solid sticks or cakes, mention may be made of aqueous or alcoholic types, and dry and anhydrous types.

In another alternative, the cosmetic composition is a cleansing and/or a makeup removal cosmetic composition commonly used to clean keratin materials, in particular the skin, in particular when they are covered with makeup products such as a foundation. These compositions generally contain a liquid or solid soap base. The term "soap" as such designates the fatty acid neutralized by a mineral base or fatty acid salt. The fatty acid is often a carboxylic acid that comprises a linear or branched alkyl chain, saturated or unsaturated, having from 6 to 30 carbon atoms, advantageously from 12 to 22 carbon atoms. Soaps are generally fatty acid soaps of tallow and/or coconut and/or castor. Preferably these soaps are chosen from sodium slats in particular from $C_{16}$-$C_{20}$ fatty acid sodium salts and $C_{10}$-$C_{14}$ fatty acid sodium salts or mixtures thereof. In particular, the soap contains a sodium stearate.

In yet another alternative, the cosmetic composition is a hybrid powder.

A composition according to the invention may be a cast powder.

Hybrid powders can comprise a dispersion of generally spherical particles of at least one surface-stabilized polymer, in a physiologically and cosmetically acceptable liquid fatty body.

These dispersions can in particular have the form of nanoparticles of polymers in stable dispersion in said fatty body. The nanoparticles are preferably of a size between 5 nm and 600 nm.

Radical polymers, polycondensates, and even polymers of natural origin can as such be used. The polymer can be chosen by those skilled in the art according to its properties, according to the subsequent application desired for the composition.

As such, the polymer can be film-forming or non-film-forming; in this second case, it can in particular have the form of a crosslinked polymer.

It is therefore possible to use film-forming polymers, preferably having a low glass transition temperature (Tg), less than or equal to ambient temperature.

It is also possible to use non-film-forming polymers, optionally crosslinked, which can be used as fillers dispersed in a stable manner in an oil.

The polymers that can be used in the context of this invention preferably have a molecular weight of about 2,000 to 10,000,000, and a glass transition temperature of −100° C. to 300° C. When the polymer has a Tg that is too high for the desired application, it can be combined with a plasticizer so as to lower the Tg of the mixture used. The plasticizer can be chosen from the standard plasticizers used in the field of application and in particular from the components that can be solvents of the polymer.

Of the crosslinked film-forming polymers, mention may be made of radical, acrylic or vinyl homopolymers or copolymers, preferably with a Tg less than or equal to 30° C. Of the non-film-forming polymers, mention may be made of radical, vinyl or acrylic homopolymers or copolymers, optionally crosslinked, preferably having a Tg greater than or equal to 40° C., such as methyl polymethacrylate, polystyrene or tert-butyl polyacrylate.

The liquid fatty body in which the polymer particles are dispersed, can be formed from any cosmetically or dermatologically acceptable oil, in particular chosen from carbon, hydrocarbon, fluorinated and/or silicone oils of mineral, animal, plant or synthetic origin, alone or in a mixture to the extent that they form a homogeneous and stable mixture and that they are compatible with the envisaged use.

"Liquid fatty body" means any non-aqueous liquid medium at ambient temperature. Mention can as such be made of hydrocarbon oils, acid esters, higher fatty acids, silicone oils optionally phenylated or optionally substituted with aliphatic and/or aromatic groups, optionally fluorinated, or with functional groups such as hydroxyl, thiol and/or amine groups; polysiloxanes modified by fatty acids, fatty alcohols or polyoxyalkylenes, fluorinated silicones, perfluorinated oils. Volatile oils can also be used.

A hybrid powder can comprise at least one non-polymeric molecular organic gelling agent, also referred to as organogelator, which is a compound of which the molecules are able to establish physical interactions between them that lead to a self-aggregation of the molecules with the forming of a three-dimensional supra-molecular network which is responsible for the gelification of the oil(s) (also referred to as liquid fatty phase). The supra-molecular network can result from the forming of a network of fibrils (due to the stackings or aggregations of organogelator molecules), immobilizing the molecules of the liquid fatty phase. The ability to form this network of fibrils, and therefore to gel, depends on the nature (or chemical class) of the organogelator, on the nature of the substituents carried by its molecules for a given chemical class and on the nature of the liquid fatty phase.

In general, each molecule of an organogelator can establish several types of physical interactions with a nearby molecule. Also, advantageously, the molecules of the organogelators according to the invention comprise at least one group able to establish hydrogen bonds and better at least two groups able of establishing hydrogen bonds, at least one aromatic cycle and better at least two aromatic cycles, at least one or several ethylene unsaturation bonds and/or at least one or several asymmetric carbons.

Preferably, the groups able to create hydrogen bonds are chosen from the hydroxyl, carbonyl, amino, carboxylic acid, amide, urea, benzyl groups and their associations. The organogelator or organogelators according to the invention are soluble in the liquid fatty phase after heating until the obtaining of a transparent homogeneous liquid phase. They can be solid or liquid at ambient temperature and atmospheric pressure.

Among these organogelators, mention can in particular be made of carboxylic acid amides, with the diamides having hydrocarbon chains each containing from 1 to 22 carbon atoms, for example from 6 to 18 carbon atoms, said chains being non-substituted or substituted with at least one substituent chosen from the ester, urea and fluoro groups (see application EP-A-1086945) and in particular the diamides resulting from the reaction of diaminocyclohexane, with the amides of N-acylamino acids such as the diamides resulting from the action of an N-acylamino acid with the amines comprising 1 to 22 carbon atoms. Compounds of the bis-urea type can also used as organogelators.

Examples of organogelators are dibutyl lauroyl glutamide and dibutyl ethylhexanoyl glutamide.

The hybrid powder can be a fatty powder comprising typically 40 to 50 wt % fatty bodies, 35 to 45 wt % nacre or pigment, and 5 to 20 wt % of a polymer by mass in relation to the total mass of the composition.

The expression "fatty binder" designates a fatty body or a mixture of fatty bodies forming the binder of the compact or cast powders, as well as a fatty body or mixture of fatty bodies present in the loose powders in particular in order to increase the gentleness of application and favor adherence on the skin.

The use as binding agents, in a compact powder, of silicone oils, which are linear polysiloxanes (polydimethylsiloxane or similar, abbreviated as PDMS) with low viscosity, combined with PDMS of high viscosity (silicone gums), is described in patent application JP-61-180707.

The use as binders of silicone resins (products of three-dimensional polycondensation) has also been recommended combined with volatile silicones, in cosmetic product.

The manufacturing method according to the invention is implemented in an apparatus 50 via the manufacture by direct deposit of successive layers, of which an example is diagrammatically shown in FIG. 1.

The apparatus 50 comprises a formation assembly of layers comprising at least one nozzle 52 of distribution of at least one cosmetic material in liquid form, and, for each cosmetic material distributed by the nozzle 52, a packaging container 54 of the cosmetic material, et a conveying assembly 56 of the cosmetic material between the container 54 and the nozzle 52.

The apparatus 50 comprises a substrate surface 58, able to carry the layers of cosmetic material deposited successively on each other, and an assembly 60 of relative displacement of the nozzle 52 with respect to the substrate surface 58.

The apparatus 50 also comprises a control unit 62 for the displacement assembly 60 and for the conveying assembly 56. It advantageously comprises a man-machine interface 64.

In this example, the apparatus 50 comprises a nozzle 52 combined with each container 54, in order to deliver the cosmetic material contained in the container 54.

Alternatively, at least two containers 54 are connected to the same nozzle 52.

The nozzle 52 defines at least one dispensing orifice of cosmetic material. Advantageously, it is able to distribute the cosmetic material in the form of successive droplets which are sprayed towards the substrate surface 58 on the substrate surface 58 or onto a previous layer.

Each droplet preferably has a mass less than 100 ng, and is for example between 30 ng and 100 ng. The distance separating the dispensing orifice of the previous layer is preferable less than 5 mm, and is in particular between 0.5 mm and 1.5 mm.

As such, each droplet or set of droplets sprayed at a given position of the nozzle 52 is able to define an area of the layer 19 forming a "pixel" on the layer to be deposited.

The composition and/or the appearance of each pixel can as such be defined by the nature of the cosmetic material or materials added to the pixel.

Each container 54 is advantageously provided with a heating system 66 able to maintain the cosmetic material in liquid form in the container 54, and advantageously with a stirrer (not shown).

The conveying assembly 56 comprises a duct 70 for the intake of cosmetic material, connecting the container 54 to the nozzle 52, a system (not shown) for pumping cosmetic material through the duct 70, and at least one control element 72 for the flow of the cosmetic material flowing through the intake duct 70, controlled by the unit 62. The control element 72 is for example a valve controlled between a configuration for blocking the flow of cosmetic material and a configuration for the distribution of cosmetic material. In one alternative, the conveying assembly 56 is devoid of a control element 72, with the flow of the cosmetic material being controlled by the pumping system.

Preferably, the duct 70 and the nozzle 52 are thermally insulated in order to maintain the cosmetic material in liquid form during its conveyance.

The displacement assembly 60 is able to allow for the relative positioning according to three axes of the nozzle 52 with respect to the substrate surface 58, or with respect to the previous layer 19 deposited on the substrate surface 58.

The displacement assembly 60 is controlled by the unit 62 in order to horizontally displace the nozzle 52 with respect to the previous layer 19 or with respect to the substrate surface 58, in order to selectively deposit at least one droplet of cosmetic material at a predetermined location on the layer being formed, corresponding to a pixel such as defined hereinabove.

The displacement assembly 60 is furthermore controlled in order to vertically maintain the vertical distance between the nozzle 52 and the support surface 58 or the previous layer.

In this example, the displacement assembly 60 comprises a mechanism 74 for the three-dimensional displacement of the nozzle 52, and a mechanism 76 for the vertical displacement of the substrate surface 58.

The control unit 62 is able to calculate, using a digital model of the three-dimensional object, the spatial arrangement of each layer 19 to be formed by depositing using the or each nozzle 52, and, within each layer 19 to be formed, the exact composition of each area of the layer.

On this basis, the control unit 62 is able to control the corresponding relative displacement of each nozzle 52 in relation to the substrate surface 58 in order to deposit a given material onto each zone to be former of each layer 19, and control the controlling of the conveying assembly 56, in particular the pumping system and the control element 72, at each position of the nozzle 52, according to the desired material in this area.

The man-machine interface 64, when it is present, is able to allow a user to define the shape of a three-dimensional object to be create, for example by selection of a digital model file in a database of of digital models, or by importing a predefined digital model file, with a view to its use by the control unit 62.

According to the invention, the apparatus 50 comprises a source 90 of radiation able to activate the photoactivatable material present in each layer 19 that contains it.

The source of radiation 90 is for example mobile jointly with the nozzle 52, and being advantageously carried by the nozzle 52. In this case, The source of radiation 90 is preferably able to be activated by pulses before each displacement of the nozzle 52 between two positions opposite the layer 19 being formed.

As indicated hereinabove, the source 90 is able to emit a suitable radiation for the crosslinking at a wavelength between 210 nm and 600 nm, preferably between 250 nm and 400 nm.

In one preferred embodiment of the invention, the source 90 is a UV lamp and particularly a mercury vapor lamp, optionally doped with further elements, such as gallium, suitable for modifying the emission spectrum of the light source 90. Alternatively or in addition, the source 90 comprises a laser.

An example method for producing according to the invention will now be described.

Advantageously, the user initially defines using the man-machine interface 64 the shape of the composition of the object to be created, by example by choosing a digital model file in the database of digital models or by importing this file.

Then, the digital model file is sent to the control unit 62. The control unit 62 then defines the shape of the different layers 19 intended to form the three-dimensional object, and within each layer the composition of each area of the layer defining a "pixel".

The control unit 62 then calculates the displacement required for the or each nozzle 52 during the construction of each layer 19, and determines if a cosmetic material must be added at a given position of the nozzle 52 and where applicable, what cosmetic material(s) must be added at each given position of the nozzle 52.

Each cosmetic material is prepared in a container 54 by causing the melting of the structuring agent. The cosmetic material is maintained in liquid state, advantageously using the heating system 66.

The photoactivatable material is attached to at least one cosmetic material introduced into a container 54 or is prepared in the form of a particular material introduced into a container 54 that is proper to this material.

Then, the control unit 62 controls the displacement assembly 60 and the conveying assembly 50 based on the calculations made previously in order to successively form the various layers 19 on each other.

For each layer 19 to be formed, the control unit displaces the nozzle 52 in each area to be formed of the layer 19 and sprays at least one cosmetic material, advantageously in the form of liquid droplets, against the previous layer 19 or against the substrate surface 58 where applicable, in order to form a new layer 19.

In particular, the or each structuring agent contained in each cosmetic material is deposited in the molten state in order to form the layer 19.

At least one portion of the droplets deposited contain or are formed of photoactivatable material.

The droplets are sprayed directly onto the previous layer 19 or against the substrate surface 58. The space located between the nozzle orifice 52 and the previous layer 19 is then entirely empty. In particular, this empty space is entirely devoid of material.

Between each displacement of the nozzle 52 with respect to the previous layer 19, the source of radiation 90 is activated in order to cause the activation of the photoactivatable material, via photochemical and/or thermal decomposition of the photoinitiator and by radical reaction of the monomer or monomers and/or of the prepolymer or prepolymers and/or of the polymer or polymers.

During this operation, the control unit 62 substantially maintains constant the vertical distance between the nozzle 52 and the previous layer 19 and/or the substrate surface 58.

As such the layer formed 19 is plane. "Plane" advantageously means that the maximum thickness of the layer 19 is less than 4 times the average thickness of the layer 19.

The cosmetic material at least partially solidifies by cooling, and/or by crosslinking in order to solidify the layer 19.

The cooling advantageously changes the cosmetic material to a temperature less than the temperature that it had when it was deposited. This temperature is preferably less than the melting point of the cosmetic material.

The temperature loss of the cosmetic material during cooling is greater than 3° C., in particular greater than 5° C.

Once the layer 19 is formed, displacement assembly 60 is controlled in order to separate the nozzle 52 from the previously formed layer 19. The preceding operations are repeated in order to add the different layers 19 on each other.

It is as such possible to construct three-dimensional objects 10 that comprise or are formed from a cosmetic composition having chosen and complex forms, different compositions and appearances according to the area, shadings of appearance and composition, through the simple local control of the cosmetic material to be added in each area of a given layer 19 of the three-dimensional object 10.

In an alternative, at least one material is intended solely for the construction of the three-dimensional object 10, with this cosmetic material being removed from the three-dimensional object at the end of the additive method, for example via dissolution in a suitable solvent or via melting, without affecting the three-dimensional object 10. This material is for example intended for the manufacture of undercut portions of the three-dimensional object 10.

This substrate material is for example a hydrogenated wax or a paraffin advantageously with a melting point less than 50° C.

Alternatively, this material is removed via a mechanical action, for example by being broken or scraped.

Such a material can be used to create empty areas of materials in the three-dimensional object 10, after the removal thereof.

In an alternative, at least one substrate material added in at least one layer 19 is intended to form a substrate 18 of the cosmetic composition which is a part of the three-dimensional object 10. Advantageously the substrate 18 formed as such cannot be restored after solidification, conversely to the cosmetic composition.

In this alternative, at least one partially liquid layer comprising a substrate material is deposited during the forming of the three-dimensional object. This layer is either formed of substrate material, or comprises areas formed of substrate material and areas formed of cosmetic material.

In this case, the apparatus 50 comprises at least one container 54 for the packaging of the substrate material and a conveying assembly 56 of the substrate material between the container 54 and the nozzle 52.

The control unit 62 is able to determine if the substrate material must be added at a given position of the nozzle 52, as a complement or as a replacement for a cosmetic material.

The substrate material is for example a polymer, in particular a thermoplastic polymer, a hydrogenated wax or a paraffin which is brought above its melting point during the depositing of the layer, or a non-recoverable photoactivatable polymer, taken from a family such as defined hereinabove.

The crosslinked substrate material under the effect of the illumination and/or the heating generated by the source 90 in order to form the substrate 18.

In a particular example, the substrate material is formed of a non-recoverable photoactivatable material such as defined hereinabove, which crosslinks during the forming of the three-dimensional object 10. The cosmetic composition 12 can then contain at least one recoverable photoactivatable material or not contain one.

Advantageously, the manufacturing method according to the invention is implemented for the creation of prototypes of three-dimensional objects comprising or formed of a structured cosmetic composition.

Alternatively, the manufacturing method according to the invention is implemented for the creation in production of finished products, for example in a factory or in a store.

The invention claimed is:

1. The method for the additive manufacture of a three-dimensional object comprising or forming a cosmetic composition, the method comprising the following steps:
   (a) supplying at least one cosmetic material and supplying at least one photoactivatable material;

(b) forming a layer comprising one or a plurality of cosmetic materials supplied in step (a) and on at least a first region of the layer, a photoactivatable material supplied in step (a);
(c) illuminating at least the first region of the layer to activate the photoactivatable material;
(d) forming an additional layer comprising one or a plurality of cosmetic materials supplied in step (a) and, on at least a second region of the additional layer, a photoactivatable material supplied in step (a), the additional layer at least partially covering the previous layer;
(e) illuminating at least the second region of the additional layer to activate the photoactivatable material;
(f) repeating steps (d) to (e) until the three-dimensional object is formed,
the cosmetic composition comprised in the three-dimensional object or forming the three-dimensional object being recoverable after the three-dimensional object is formed.

2. A method according to claim 1, wherein the photoactivatable material comprises a photoinitiator and a photocrosslinkable compound capable of being activated by the photoinitiator.

3. A method according to claim 2, wherein the photocrosslinkable compound comprises at least one monomer, and/or at least one prepolymer and/or at least one polymer, particularly chosen from polyesters with unsaturation(s) or (meth)acrylate groups, polyurethanes and/or polyureas with (meth)acrylate groups, polyethers with (meth)acrylate groups, epoxyacrylates, polyorganosiloxanes with (meth)acrylate or (meth)acrylamide groups, perfluoropolyethers with acrylate groups, a polyene associated with a polythiol, the mixtures thereof or copolymers thereof.

4. A method according to claim 1, wherein the photoactivatable material is deposited in liquid form via a nozzle on the first region and/or on the second region.

5. A method according to claim 4, wherein depositing the photoactivatable material comprises positioning the nozzle in a succession of given positions on the first region and/or on the second region,
and, in each given position, depositing a given quantity of photoactivatable material, illuminating the photoactivatable material deposited in the given position, and moving the nozzle to another given position on the first region and/or on the second region.

6. A method according to claim 1, wherein a first cosmetic material supplied in step (a) has a first color, a second cosmetic material supplied in step (a) having a second color, the cosmetic composition formed comprising first cosmetic material and second cosmetic material on the same layer or on different layers.

7. A method according to claim 1, wherein the photoactivatable material is included in or forms a cosmetic material intended to be deposited in liquid form.

8. A method according to claim 1, wherein at least one layer comprises a photoactivatable substrate material suitable for forming a substrate of the cosmetic composition, the substrate being non-recoverable, the method comprising illuminating the photoactivatable substrate material to form at least a part of the substrate.

9. A method according to claim 1, wherein, in step (a), at least one cosmetic material contains at least one structuring agent in liquid form, the method comprising a preliminary step for heating the cosmetic material(s) supplied in step (a) in order to melt the or each structuring agent;
each layer formed in step (b) comprising one or a plurality of heated cosmetic materials, the or each structuring agent contained in the cosmetic material(s) being deposited in the molten state;
the layer being at least partially solidified by cooling the or each cosmetic material to a temperature below that of the or each cosmetic material deposited in step (b);
each additional layer formed in step (d) comprising one or a plurality of heated cosmetic materials, the or each structuring agent contained in the cosmetic material(s) being deposited in the molten state;
the additional layer being at least partially solidified by cooling the or each cosmetic material to a temperature below that of the or each cosmetic material deposited in step (c);
the photoactivatable material being deposited in at least one at least partially liquid layer.

10. A method according to claim 9, wherein the structuring agent is chosen from waxes, organophilic clays, pyrogenic silicas, fatty acids, pasty compounds, gelling agents, thickening agents, glutamide resins, hydrophobic celluloses, tackifying resins, and mixtures thereof.

11. A method according to claim 10, wherein the precursor material of the cosmetic composition comprises a mass wax content greater than 10%.

12. A method according to claim 9, wherein the three-dimensional object is a lipstick, a stick, a hybrid powder, a deodorant and/or antiperspirant product, a soap, a face mask, a hair styling wax, and/or a solid perfume.

13. The method according to claim 2, wherein the photoactivatable material is deposited in liquid form via a nozzle on the first region and/or on the second region.

14. The method according to claim 3, wherein the photoactivatable material is deposited in liquid form via a nozzle on the first region and/or on the second region.

15. A method according claim 2, wherein a first cosmetic material supplied in step (a) has a first color, a second cosmetic material supplied in step (a) having a second color, the cosmetic composition formed comprising first cosmetic material and second cosmetic material on the same layer or on different layers.

16. A method according claim 3, wherein a first cosmetic material supplied in step (a) has a first color, a second cosmetic material supplied in step (a) having a second color, the cosmetic composition formed comprising first cosmetic material and second cosmetic material on the same layer or on different layers.

17. A method according claim 4, wherein a first cosmetic material supplied in step (a) has a first color, a second cosmetic material supplied in step (a) having a second color, the cosmetic composition formed comprising first cosmetic material and second cosmetic material on the same layer or on different layers.

* * * * *